United States Patent
Munt et al.

(10) Patent No.: US 10,613,011 B2
(45) Date of Patent: Apr. 7, 2020

(54) DIFFUSION CELLS AND RELATED METHODS

(71) Applicant: Creighton University, Omaha, NE (US)

(72) Inventors: Daniel Munt, Omaha, NE (US); Alekha Dash, Omaha, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 15/457,730

(22) Filed: Mar. 13, 2017

(65) Prior Publication Data

US 2018/0259438 A1 Sep. 13, 2018
US 2020/0064247 A9 Feb. 27, 2020

Related U.S. Application Data

(60) Provisional application No. 62/307,750, filed on Mar. 4, 2016.

(51) Int. Cl.
*G01N 13/00* (2006.01)
*G01N 33/15* (2006.01)

(52) U.S. Cl.
CPC ............ *G01N 13/00* (2013.01); *G01N 33/15* (2013.01); *G01N 2013/003* (2013.01)

(58) Field of Classification Search
CPC ... G01N 13/00; G01N 33/15; G01N 2013/003
See application file for complete search history.

(56) References Cited

U.S. PATENT DOCUMENTS

| 4,594,884 | A | * | 6/1986 | Bondi | G01N 13/00 210/321.84 |
| 4,740,309 | A | * | 4/1988 | Higuchi | B01D 61/28 210/321.63 |
| 4,958,529 | A | * | 9/1990 | Vestal | G01N 30/7273 250/288 |
| 5,116,577 | A | * | 5/1992 | Eickeler | G01N 31/223 422/401 |
| 5,198,109 | A | * | 3/1993 | Hanson | G01N 13/00 210/321.75 |
| 2005/0063862 | A1 | * | 3/2005 | Roscoe | B01L 3/5025 422/68.1 |

OTHER PUBLICATIONS

'particlescience.com' [online]. "Development and Validation of In Vitro Release Testing Methods for Semisolid Formulations," Technical Brief, vol. 10, 2009, 2 pages, Retrieved from the Internet: URL <http://www.particlesciences.com/docs/technical_briefs/TB_10.pdf.
'permegear.com' [online]. "Diffusion Testing Fundamentals," 8 pages, Retrieved from the Internet: URL <http://permegear.com/wp-content/uploads/2015/08/primer.pdf.

* cited by examiner

*Primary Examiner* — Xin Y Zhong
(74) *Attorney, Agent, or Firm* — Fish & Richardson P.C.

(57) ABSTRACT

A method of performing a diffusion test includes clamping a membrane to a body such that a first surface of the membrane is in fluid communication with an interior chamber of the body and a second surface of the membrane is exposed to ambient air, flowing a substance through the ambient air such that at least a portion of the substance lands on the second surface while the membrane is vertically oriented, and determining a concentration of the substance in the interior chamber after some of the substance has diffused through the membrane.

20 Claims, 12 Drawing Sheets

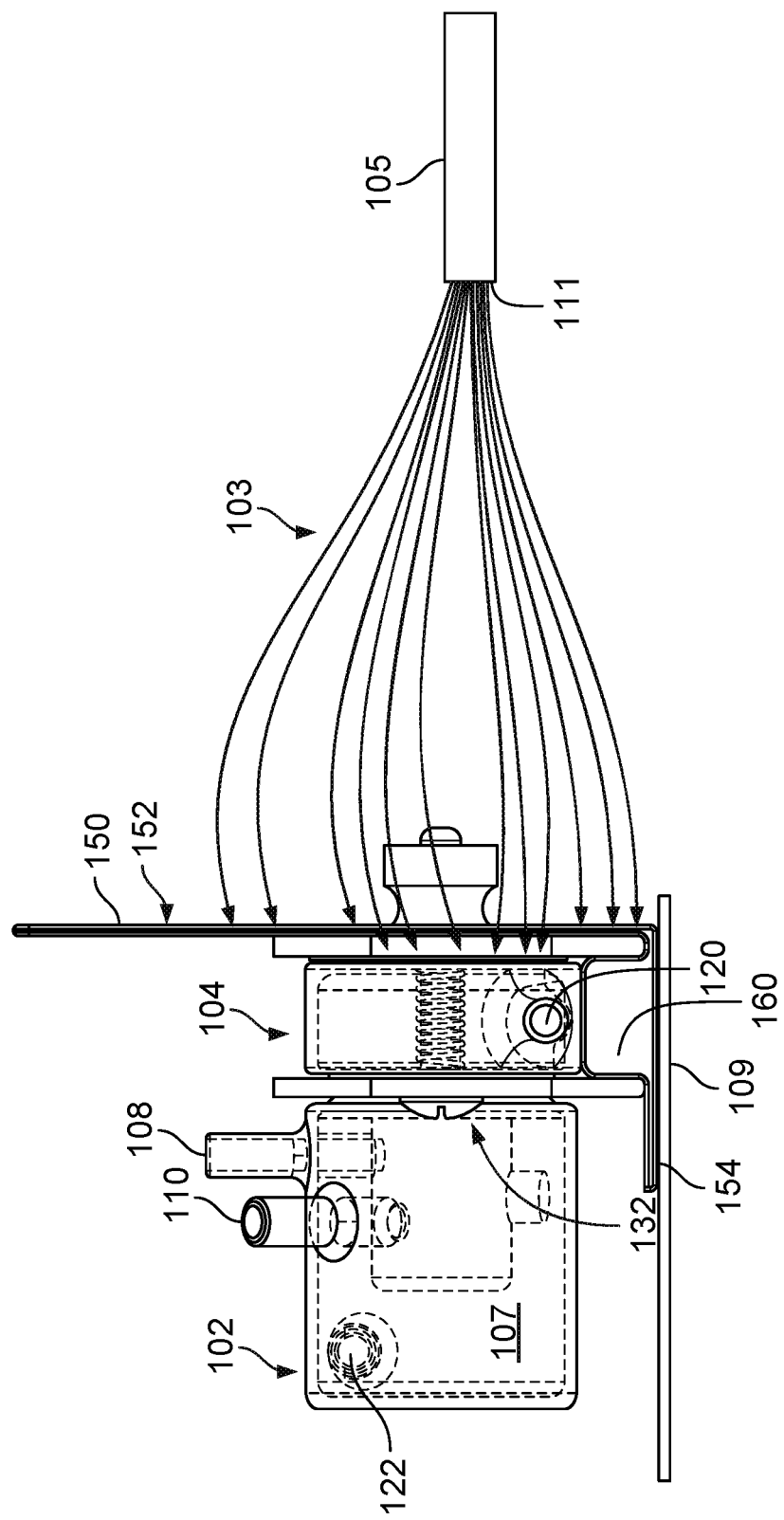

200

202
Clamping a Membrane to a Body Such that a First Surface of the Membrane is in Fluid Communication with an Interior Chamber of the Body and a Second Surface of the Membrane is Exposed to Ambient Air 204
Flowing a Substance Through the Ambient Air Such that at Least a Portion of the Substance Lands on the Second Surface While the Membrane is Vertically Oriented 206
Determining a Concentration of the Substance in the Interior Chamber After some of the Substance has Diffused Through the Membrane

FIG. 12

DIFFUSION CELLS AND RELATED METHODS

TECHNICAL FIELD

This disclosure relates to diffusion cells and associated methods of performing diffusion tests, such as diffusion tests for examining the movement of airborne substances (e.g., sprayed or aerosolized substances) through materials.

BACKGROUND

Development of substances used in a variety of applications often requires an understanding of how the substances move through materials. For example, an ability of a substance (e.g., drugs, chemicals treatments, and various particulates) to diffuse through a semi-permeable material construct can provide insight into an effectiveness or a toxicity of the substance, as well as characteristics of the material construct. In some implementations, diffusion cells can be used to examine such parameters.

SUMMARY

In general, this disclosure relates to diffusion cells and methods of using the diffusion cells to perform diffusion tests, such diffusion tests that examine the movement of airborne substances through semi-permeable membranes. The diffusion cells are advantageously configured and, accordingly, particularly useful for in vitro examination of diffusion characteristics of airborne substances, which may not be adequately examined using conventional diffusion cells that include liquid carrying donor chambers. An open, accessible configuration of the disclosed diffusion cells provide an air-solid interface to which a volume of an airborne substance can be delivered with a substantially even distribution across an area of a membrane secured to the diffusion cells. Accordingly, the configuration of the diffusion cells facilitates experimental acquisition of representative data that reflects a realistic application of a substance.

Furthermore, the configuration of the diffusion cells and a horizontal experimental arrangement of the diffusion cells advantageously permit examination of an airborne substance using only a small volume of a substance, which may be beneficial when the substance is only available in limited amounts or is obtained at a high cost. Additionally, the horizontal experimental arrangement and a flat donor structure of the diffusion cells prevents an airborne substance from settling and pooling on a membrane, which may otherwise occur with conventional experimental arrangements or conventional diffusion cells.

In another aspect, a method of performing a diffusion test includes clamping a membrane to a body such that a first surface of the membrane is in fluid communication with an interior chamber of the body and a second surface of the membrane is exposed to ambient air, flowing a substance through the ambient air such that at least a portion of the substance lands on the second surface while the membrane is vertically oriented, and determining a concentration of the substance in the interior chamber after some of the substance has diffused through the membrane.

Embodiments may include one or more of the following features.

In some embodiments, the method further includes preventing the substance from pooling on the membrane.

In certain embodiments, the method further includes arranging the body in a horizontal orientation prior to flowing the substance through ambient air.

In some embodiments, the method further includes assembling a splash guard with the body to prevent an airborne flow of the substance from contacting the body.

In certain embodiments, clamping the membrane to the body includes providing an air-solid interface.

In some embodiments, flowing the substance through the ambient air includes evenly distributing the substance across the second surface of the membrane.

In certain embodiments, the method further includes distributing a volume of about 2 µL/cm2 to about 20 µL/cm2 of the substance across the second surface of the membrane.

In some embodiments, the method further includes flowing a heat transfer fluid through an exterior chamber of the body that surrounds the interior chamber of the body.

In certain embodiments, the method further includes delivering a fluid buffer to the interior chamber of the body.

In some embodiments, the method further includes introducing the fluid buffer into a port located above the interior chamber of the body.

In certain embodiments, the method further includes withdrawing a sample of the fluid buffer from the interior chamber of the body at multiple predetermined times after at least the portion of the substance has landed on the second surface of the membrane.

In some embodiments, determining the concentration of the substance in the interior chamber includes determining respective concentrations of the substance in the fluid buffer following the multiple predetermined times.

In certain embodiments, the method further includes determining one or more diffusion parameters associated with one or both of the substance and the membrane based on the respective concentrations.

In some embodiments, flowing the substance through the ambient air includes flowing an aerosolized substance towards the membrane.

In certain embodiments, flowing the substance through the ambient air includes spraying the substance towards the membrane.

In some embodiments, flowing the substance through the ambient air includes flowing nanoparticles towards the membrane.

In certain embodiments, flowing the substance through the ambient air includes flowing a drug towards the membrane.

In some embodiments, flowing the substance through the ambient air includes flowing a chemical that is toxic to animals towards the membrane.

In certain embodiments, clamping the membrane to the body includes securing a construct including one or both of an artificial tissue and a natural tissue to the body.

In another aspect, a diffusion cell includes a body defining an interior chamber and an adjustable clamp configured to secure a membrane to the body across an open end of the interior chamber, wherein the adjustable clamp defines a beveled edge configured to prevent pooling of a substance on the membrane.

Embodiments may include one or more of the following features.

In some embodiments, the diffusion cell includes one or more seals located between the body and the adjustable clamp.

In certain embodiments, the diffusion cell includes a guard configured to engage one or both of the body and the adjustable clamp to block the flow of the substance.

In some embodiments, the diffusion cell provides an air-solid interface.

In some embodiments, the body defines an exterior chamber that surrounds the interior chamber.

In certain embodiments, the exterior chamber provides a liquid jacket for heating and cooling the interior chamber.

In some embodiments, the body defines an inlet port and an outlet port for flowing a heat transfer fluid through the exterior chamber.

In certain embodiments, the body defines one or more sample ports for delivering a fluid buffer to and withdrawing a fluid buffer from the interior chamber.

In some embodiments, the adjustable clamp includes one or more threaded fasteners for securing a frontal plate of the adjustable clamp to the body.

In certain embodiments, the frontal plate defines the beveled edge.

In some embodiments, the beveled edge surrounds an opening in the frontal plate through which the substance can flow to the membrane.

Other aspects, features, and advantages will be apparent from the description, the drawings, and the claims.

DESCRIPTION OF DRAWINGS

FIG. 11 is a side view of a diffusion system including the diffusion cell of FIG. 1 and the splash guard of FIG. 9, arranged with a dosage source to carry out a diffusion test.
FIG. 12 is a flowchart illustrating a method of using the diffusion cell of FIG. 1.

DETAILED DESCRIPTION

Figure 1:
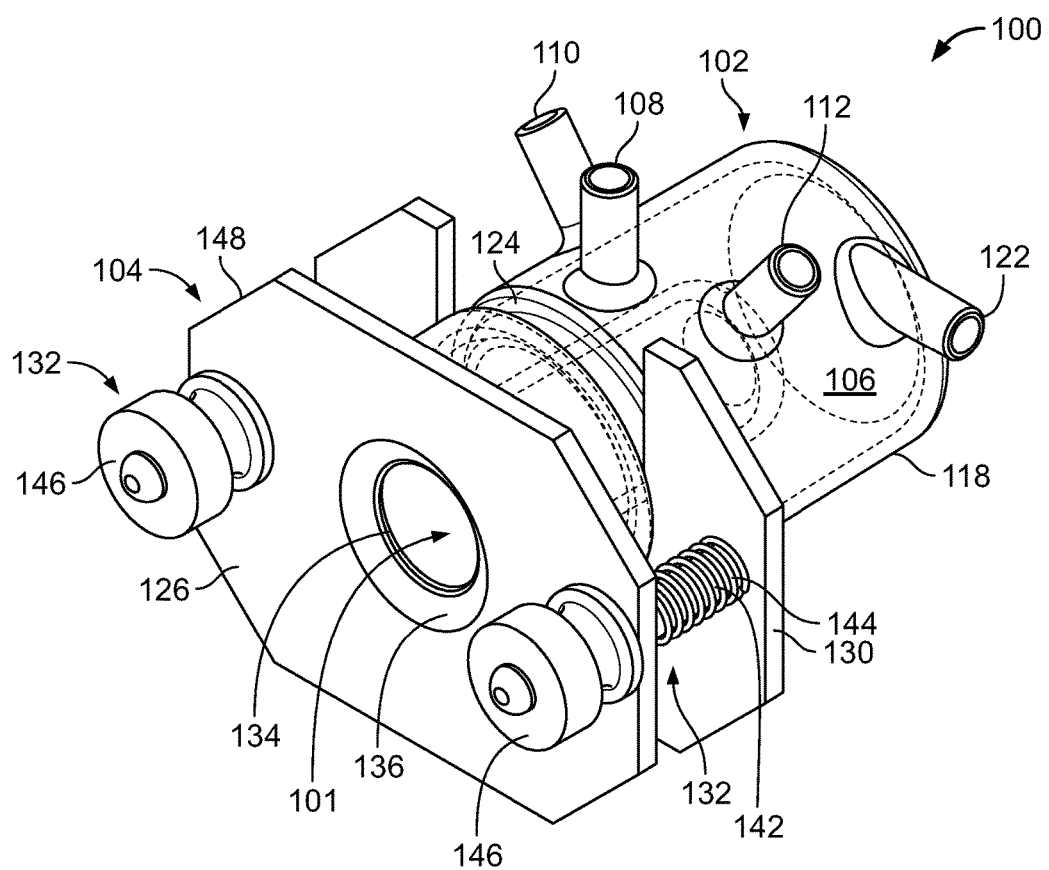
FIG. 1 is a perspective view of a diffusion cell.
Figure 2:
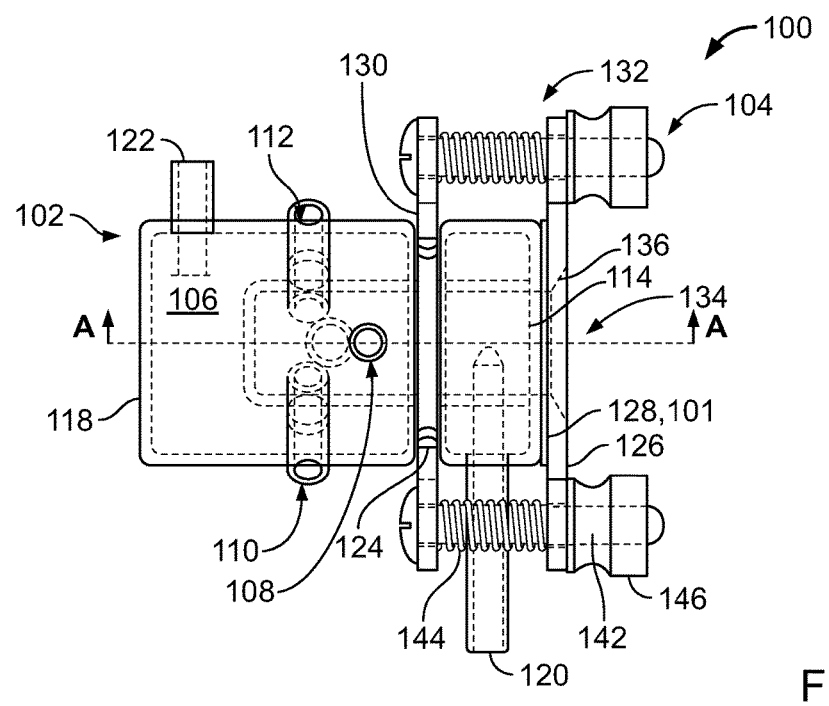
FIG. 2 is a top view of the diffusion cell of FIG. 1.
Figure 3:
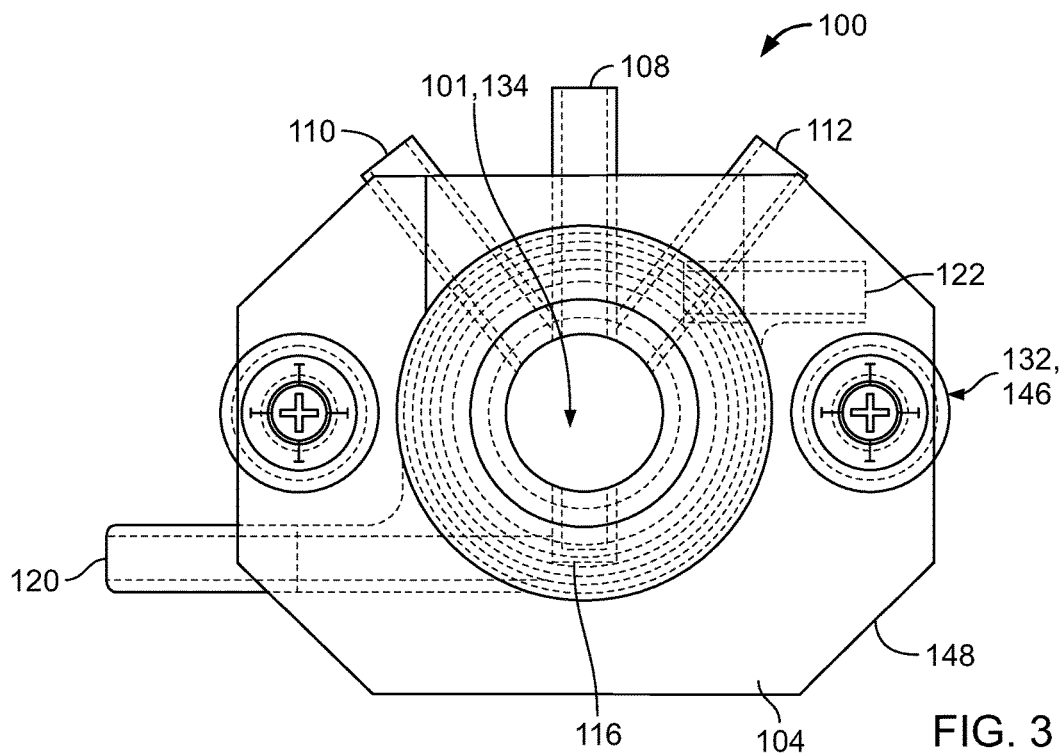
FIG. 3 is front view of the diffusion cell of FIG. 1.
Figure 4:
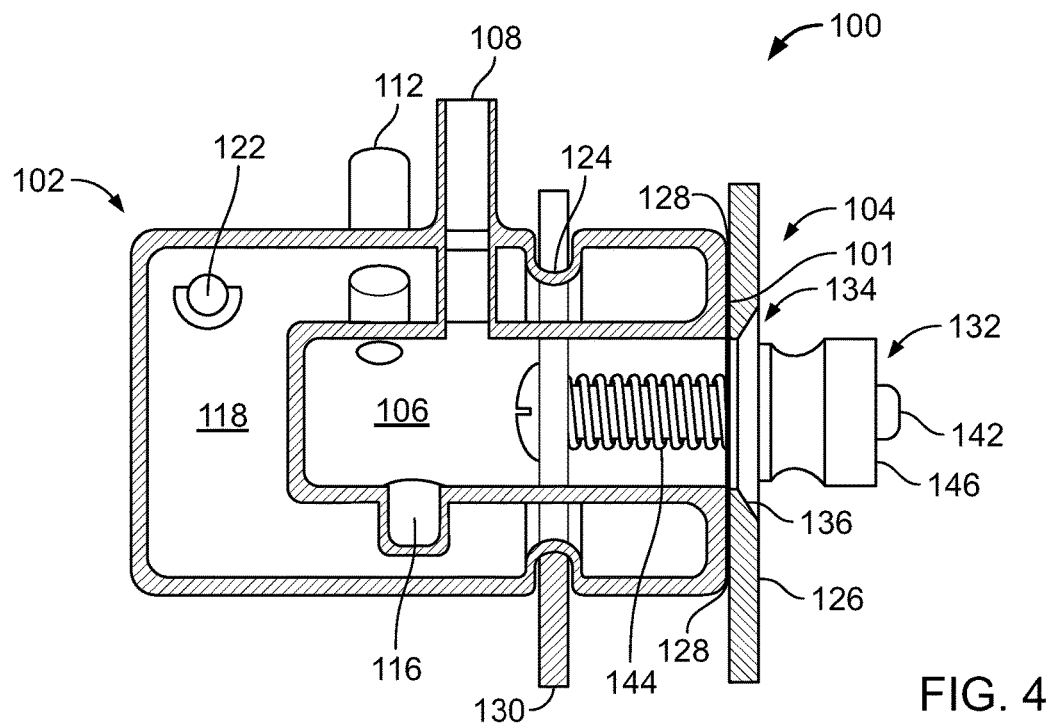
FIG. 4 is cross-sectional view of the diffusion cell of FIG. 1.
Figure 5:
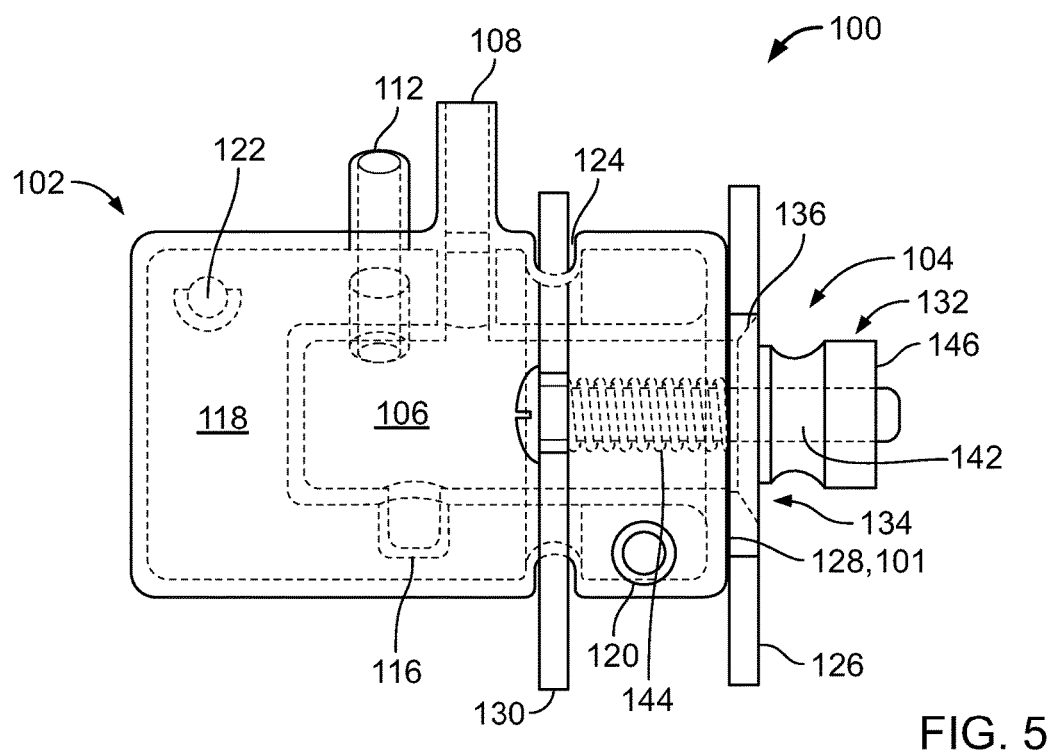
FIG. 5 is a side view of the diffusion cell of FIG. 1.

FIGS. 1-5 illustrate various views of a diffusion cell 100 (e.g., a Munt-Dash diffusion cell) used for examining movement of a substance (e.g., a permeant) through a membrane 101 (e.g., for examining penetration of the substance into and movement of the substance through the membrane 101). The diffusion cell 100 can be used for measuring parameters such as flux (e.g., an amount of permeant that crosses a membrane per unit area per unit time), accumulation (e.g., an amount of permeant that crosses a membrane within a certain time period), diffusivity (e.g., a measure of how easily a permeant penetrates a membrane, as an area per unit time), a permeability coefficient (e.g., a rate of permeant penetration per concentration, expressed as a distance per unit time), and a lag time (e.g., a time required for a permeant to permeate through a membrane and into a receptor fluid and to reach a steady state of diffusion).

The membrane 101 is a selective, semi-permeable barrier that allows passage of some components (e.g., molecules, ions, and small particles) and that prevents passage of other components based on pore sizes of the membrane 101. Example applications for which the diffusion cell 100 can be used include transdermal drug testing of patches, ointments, and other topical formulations (e.g., ultra violet (UV) radiation protection in a sunscreen), ophthalmic drug formulations, and membrane suitability as a vapor barrier, as will be discussed in more detail below. The diffusion cell 100 includes a main body 102 and a clamp 104 that secures the membrane 101 to the main body 102.

Figure 6:
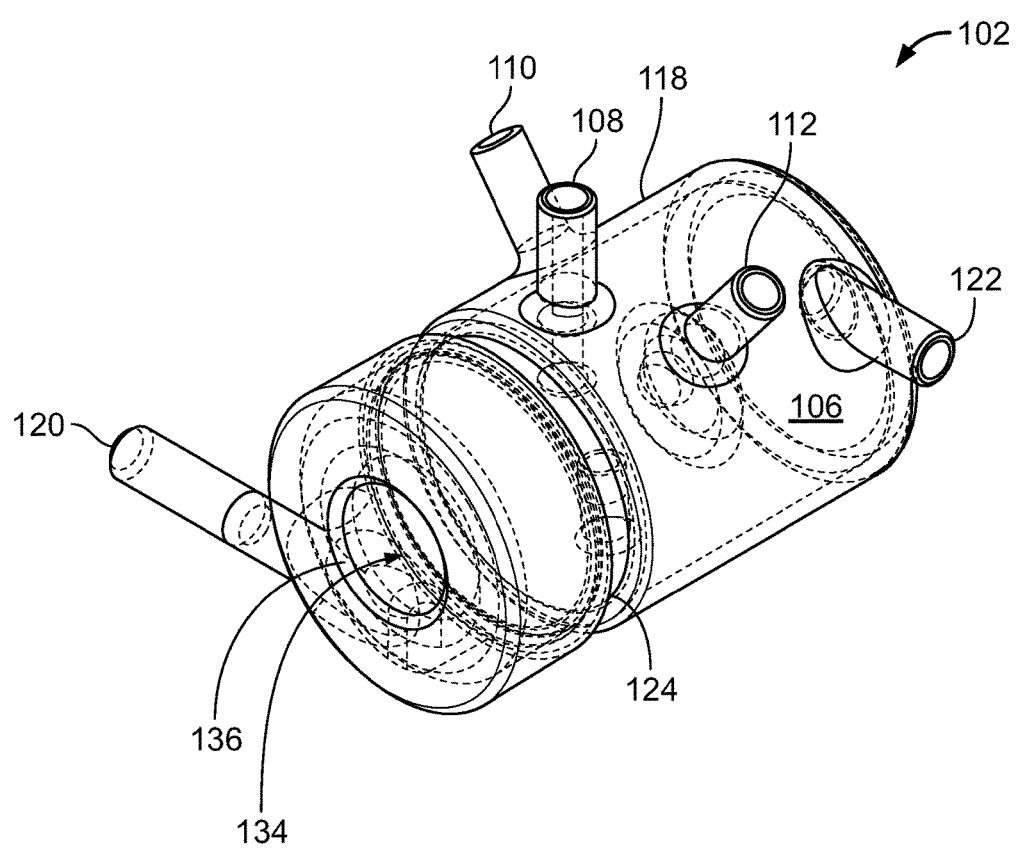
FIG. 6 is a perspective view of a main body of the diffusion cell of FIG. 1.

FIG. 6 illustrates a perspective view of the main body 102. The main body 102 defines an interior chamber 106 that serves as a receptacle (e.g., a receptor chamber) for a fluid buffer (e.g., a receptor solution) and three sample ports 108, 110, 112 that provide access to the interior chamber 106 for introducing the fluid buffer to or removing the fluid buffer from the interior chamber 106. The interior chamber 106 can be hermetically sealed by the clamp 104 at an open end 114 and at the sample ports 108, 110, 112 by any of caps, syringes, tubing, and septa, depending on a flow configuration and a sampling technique utilized for a diffusion test. The main body 102 also defines an interior recess 116 in which a magnetic stir bar (not shown) can be placed for mixing the fluid buffer within the interior chamber 106.

The main body 102 also defines an exterior chamber 118 that surrounds the interior chamber 106 and portions of the sample ports 108, 110, 112 such that the sample ports 108, 110, 112 extend through a wall of the exterior chamber 118. The exterior chamber 118 provides a liquid jacket (e.g., a water jacket) through which liquid can be flowed to transfer heat to or transfer heat away from the interior chamber 106. In this regard, the main body 102 defines an inlet port 120 located near the open end 114 of the interior chamber 106 and an outlet port 122 located near an opposite end of the main body 102. The inlet and outlet ports 120, 122 can be connected to liquid flow lines. The main body 102 further defines an exterior recess 124 along a circumference of the main body 102 and along which the clamp 104 is secured, as will be discussed in more detail below.

The main body 102 may be made of one or more chemically robust materials that are non-corrosive, that can withstand temperatures of up to about 50° C., that are transparent or translucent, that are non-reactive, and that have good thermal conductance, such as glass and polymers like polyvinylidene fluoride (PVDF), polytetrafluoroethylene (PTFE), and acrylic. The interior chamber 106 has a generally cylindrical shape. The exterior chamber 118 has a generally annular cross-sectional shape along a portion surrounding the interior chamber 106 and a generally cylindrical shape along a remaining portion. The main body 102 has a wall thickness of about 1 mm to about 5 mm (e.g., about 2 mm) along the interior and exterior chambers 106, 118. The interior chamber 106 has a length of about 2 cm to about 1] cm (e.g., about 2.5 cm) and an internal diameter of about 6 mm to about 100 mm (e.g., about 11.5 mm), such that the interior chamber 106 defines an interior volume of about 0.5 mL to about 1000 mL (e.g., about 3.5 mL) and defines a diffusion area of about 0.3 cm² to about 80 cm² (e.g., about 1.04 cm²). The exterior chamber 118 has a length of about 3 cm to about 15 cm (e.g., about 4.5 cm) and a maximum internal diameter of about 18 mm to about 120 mm (e.g., about 24 mm), such that the exterior chamber 118 defines an internal volume of about 7.6 mL to about 1700 mL (e.g., about 20 mL).

The main body 102 has a wall thickness of about 1 mm to about 5 mm (e.g., about 1.5 mm) along the sample ports 108, 110, 112 and the inlet and outlet ports 120, 122. The sample ports 108, 110, 112 have a length of about 0.5 cm to about 5 cm (e.g., about 1 cm) and an internal diameter of about 0.2 cm to about 1 cm (e.g., about 0.4 cm). The sample port 108 is located about 1.5 cm to about 5 cm (e.g., about 2.2 cm) from the open end 114 of the interior chamber 106, and the sample ports 110, 112 are located about 1.8 cm to about 7 cm (e.g., about 2.8 cm) from the open end 114 of the interior chamber 106. The sample port 108 is spaced apart from each sample port 110, 112 by an angle of about 5 degrees to about 45 degrees (e.g., about 15 degrees) around the wall of the exterior chamber 118. The inlet port 120 has a length of about 1.5 cm to about 10 cm (e.g., about 3 cm), an internal diameter of about 0.3 cm to about 2 cm (e.g., about 0.4 cm), and an outer diameter of about 0.5 cm to about 2.5 cm (e.g., about 0.7 cm). The inlet port 120 is located about 0.2 cm to about 14.5 cm (e.g., about 0.2 cm) from the open end 114 of the interior chamber 106. The outlet port 122 has a length of about 1.5 cm to about 10 cm (e.g., about 3 cm) and an internal diameter of about 0.3 cm to about 2 cm (e.g., about 0.4 cm). The outlet port 122 is located about 0.2 cm to about 14.5 cm (e.g., about 3.7 cm) from the open end 114 of the interior chamber 106. The inlet port 120 is spaced apart from the outlet port 122 by about 90 degrees to about 180 degrees (e.g., about 180 degrees) around the wall of the exterior chamber 118.

The exterior recess 124 has an outer diameter of about 1.5 cm to about 11.5 cm (e.g., about 1.9 cm). The exterior recess 124 is located about 0.7 cm to about 5 cm (e.g., about 1.2 cm) from the open end 114 of the interior chamber 106. The interior recess 116 has a diameter of about 0.3 cm to about 2.5 cm (e.g., about 0.4 cm) and a depth of about 0.1 cm to about 2.5 cm (e.g., about 0.2 cm), such that the interior recess 116 defines a volume of about 0.03 mL to about 13 mL (e.g., about 0.1 mL).

Figure 8:
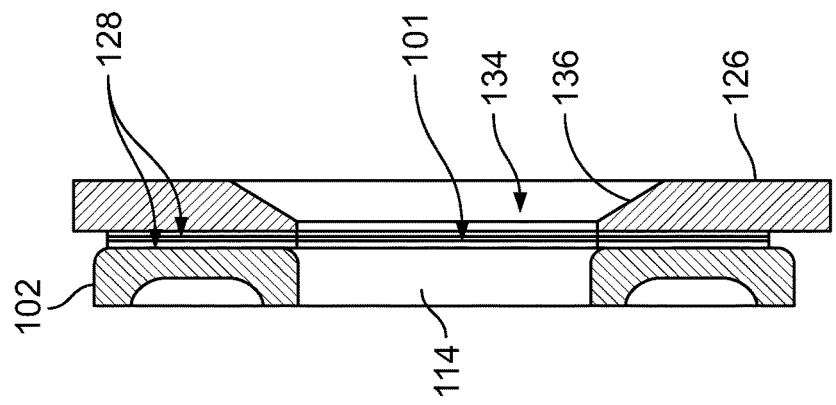
FIG. 8 is a cross-sectional view of a portion of the clamp of FIG. 7.
Figure 7:
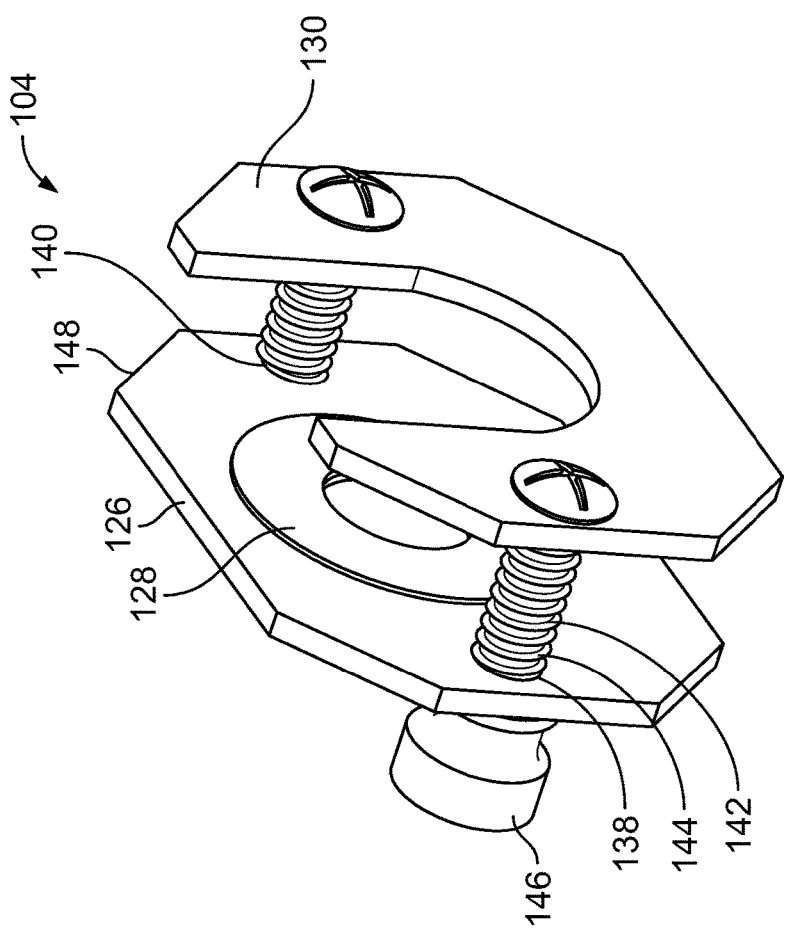
FIG. 7 is a rear perspective view of a clamp of the diffusion cell of FIG. 1.

FIG. 7 illustrates a rear perspective view of the clamp 104, and FIG. 8 illustrates cross-sectional view of a portion of the clamp 104. In addition to securing the membrane 101 to the main body 102, the clamp 104 serves as a donor port through which the substance can be delivered to the membrane 101. Referring to FIGS. 1-8, the clamp 104 includes a frontal plate 126, two gaskets 128 disposed adjacent the frontal plate 126, a rear plate 130 engaged with the exterior recess 124 of the main body 102, and two fastener assemblies 132 for adjusting the frontal plate 126 with respect to the rear plate 130 to secure the clamp 104 to the main body 102.

The frontal plate 126 has four beveled lateral edges 148 and defines a central opening 134 through which the substance can access the membrane 101. The opening 134 is surrounded by a beveled circular edge 136 within a wall of the frontal plate 126. The beveled circular edge 136 reduces a thickness of the frontal plate 126 that extends at a right angle from the central opening 134, while still allowing a surrounding portion of the frontal plate 126 to maintain a maximal strength. An inward narrowing of the beveled circular edge 136 serves to minimize the amount of material of the frontal plate 126 near the membrane 101 (e.g., to minimize a thickness of the frontal plate 126 near the membrane 101) to prevent the substance from pooling on the membrane 101 along an edge of the central opening 134 and to cause excess droplets of the substance on the frontal plate 126 to run off of the frontal plate 126 rather than settling in a place on the membrane 101 or on the frontal plate 126 where such settling could alter the study. The beveled circular edge 136 is oriented at an angle of about 10 degrees to about 45 degrees (e.g., about 30 degrees). The frontal plate 126 also defines two lateral openings 138 through which the fastening assemblies 132 extend toward the rear plate 130. The frontal plate 126 has a length of about 3 cm to about 16 cm (e.g., about 5.1 cm) and a width of about 2.2 cm to about 16 cm (e.g., about 3.8 cm). The frontal plate 126 has a thickness of about 1 mm to about 5 mm (e.g., about 2 mm). The central opening 134 of the frontal plate has a diameter of about 0.6 cm to about 10 cm (e.g., about 1.15 cm) and equals an inner diameter of the beveled circular edge 136. The beveled circular edge 136 has an outer diameter of about 0.8 cm to about 12 cm (e.g., about 1.4 cm). The openings 138 have a diameter of about 2 mm to about 15 mm (e.g., about 5 mm).

The rear plate 130 is generally u-shaped and is positioned within the exterior recess 124 of the main body 102. Accordingly, an inner curved (e.g., semi-circular) portion of the rear plate 130 has a radius of about 0.9 cm to about 5.8 cm (e.g., about 1.1 cm). The rear plate 130 also defines two lateral openings 140 through which the fastening assemblies 132 extend toward the frontal plate 128. An outer profile of the rear plate 130 generally has the shape of an outer profile of the frontal plate 126, such that the rear plate 130 has a length and a width that are equal to the length and the width of the frontal plate 126. The rear plate 130 has a thickness of about 1 mm to about 5 mm (e.g., about 2 mm). The openings 140 have a diameter of about 2 mm to about 15 mm (e.g., about 5 mm).

In operation of the diffusion cell 100, the frontal plate 126 can be tightly secured to the main body 102 using the fastening assemblies 132. Each fastening assembly 132 includes a screw 142 that abuts the rear plate 130, a spring 144 that surrounds a shaft of the screw 142, and a threaded knob 146 that can be adjusted along the shaft of the screw 142 to force (e.g., push) the frontal plate 126 towards the spring 144. The shafts of the screws 142 have a length of about 1.6 cm to about 5 cm (e.g., about 2.5 cm). The components of the fastening assemblies 132, the frontal plate 126, and the rear plate 130 may be made of one or more chemically robust materials that are non-corrosive, can withstand temperatures of up to about 50° C., that are non-reactive, that are non-fragile, and that have minimal (<1%) deformation under a working load, such as stainless steel, anodized aluminum, PTFE, PVDF, and other rigid polymers of sufficient thickness to inhibit deformation.

The gaskets 128 have an annular shape and provide seals between the clamp 104 and the main body 102. The frontal gasket 128 is located adjacent the frontal plate 126, and the rear gasket 128 is located adjacent the main body 102. The gaskets 128 are separated by the membrane 101. The gaskets 128 have an outer diameter of about 2 cm to about 12 cm (e.g., about 2.9 cm) and an inner diameter of about 0.6 cm to about 10 cm (e.g., about 1.15 cm). The gaskets 128 have a thickness of about 0.25 mm to about 2 mm (e.g., about 0.6 mm). The gaskets 128 may be made of one or more chemically robust materials that provide suitable sealing functionality, that are non-reactive, that are non-adsorbing to permeant, and that are pliable, such as PTFE foam, solid silicone, PVDF foam, silicon coated polyurethane foam, or other pliable waterproof synthetic or natural polymers.

Figure 10:
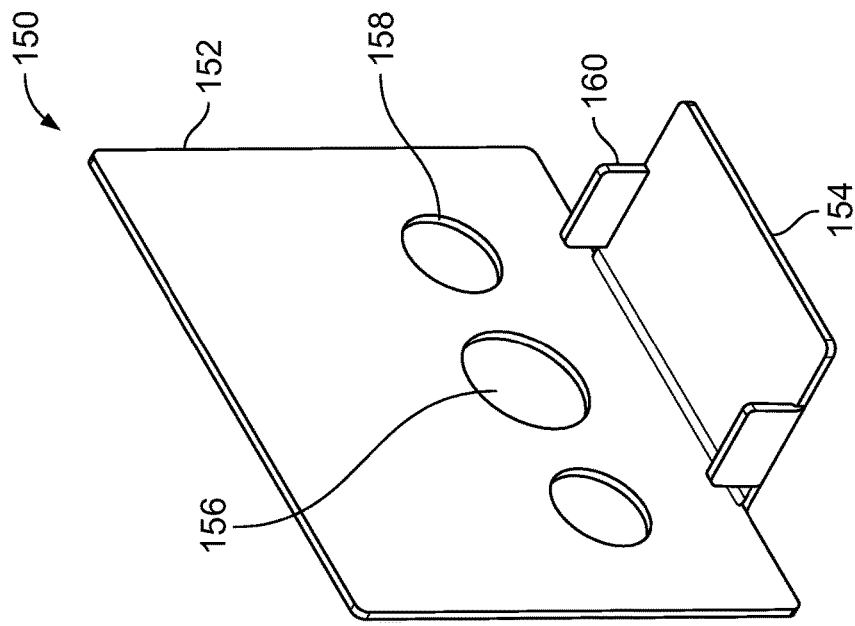
FIG. 10 is a rear perspective view of the splash guard of FIG. 9.
Figure 9:
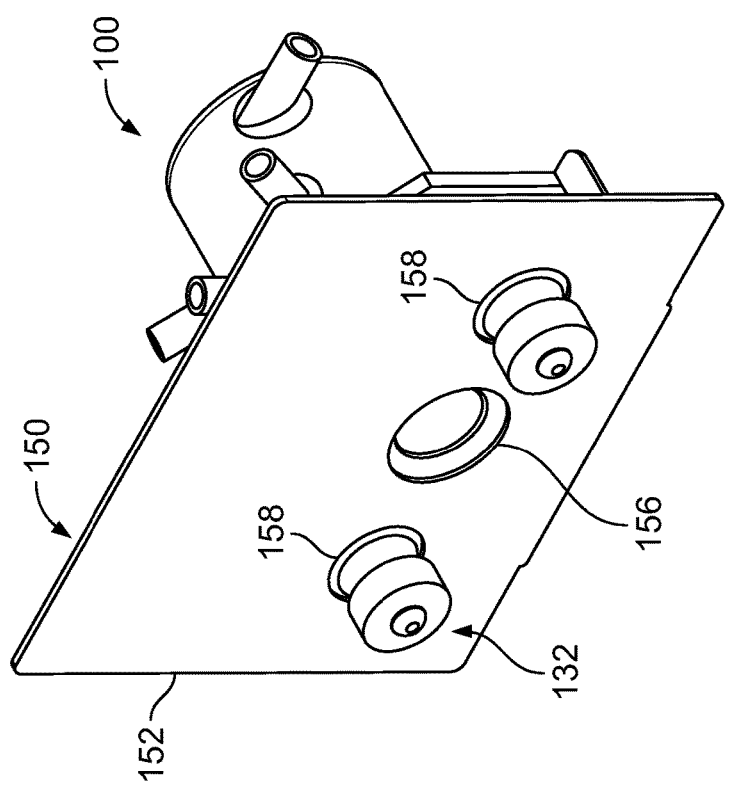
FIG. 9 is a perspective view of a splash guard attached to the diffusion cell of FIG. 1.

In some implementations, a guard can be attached to a frontal region of the diffusion cell 100 to prevent fluids from splashing rearward onto the diffusion cell 100. For example, FIG. 9 illustrates a splash guard 150 attached to the diffusion cell 100, and FIG. 10 illustrates a rear perspective view of the splash guard 150. The splash guard 150 may be a unitary structure that includes a frontal plate 152 and a base plate 154 that extends perpendicularly from the frontal plate 152.

The frontal plate 152 has a generally rectangular shape and defines a central opening 156 that aligns concentrically with the central opening 134 of the frontal plate 126 of the clamp 104 such that the central opening 156 helps to guide the substance towards the membrane 101. Accordingly, the central opening 156 has a diameter of about 0.7 cm to about 10.2 cm (e.g., about 1.2 cm). The frontal plate 152 also defines two lateral openings 158 that align concentrically with the lateral openings 138 of the frontal plate 126 of the clamp 104 to allow passage of the knobs 146. The lateral openings 158 have a diameter of about 0.5 cm to about 2.5 cm (e.g., about 1.2 cm). The frontal plate 152 has a length of about 4 cm to about 20 cm (e.g., about 6.1 cm), a width of about 4 cm to about 20 cm (e.g., about 5 cm), and a thickness of about 0.25 mm to about 2 mm (e.g., about 0.7 mm).

The base plate 154 has a generally rectangular shape and includes two tabs 160 that flank the main body 102 of the diffusion cell 100 to centrally position and lock the splash guard 150 with respect to the diffusion cell 100. The base plate 154 has a length of about 1.7 cm to about 5 cm (e.g., about 2 cm), a width of about 3 cm to about 12 cm (e.g., about 4.5 cm), and a thickness of about 0.25 mm to about 2 mm (e.g., about 0.7 mm). The tabs 160 have a length of about 0.5 cm to about 5 cm (e.g., about 1 cm), a height of about 5 cm to about 0.5 cm (e.g., about 5 cm), and a thickness of about 0.25 mm to about 2 mm (e.g., about 0.7 mm). The size and shape of the splash guard 150 can prevent an overspray of fluid from contaminating the sample ports 108, 110, 112 of the diffusion cell 100.

As discussed above, the diffusion cell 100 can be employed to examine (e.g., measure, compute, observe, visualize, or otherwise examine) diffusion characteristics of a substance through the membrane 101. The membrane 101 may be made of one or more natural or synthetic materials, such as celluloses (e.g., regenerated cellulose, nitrocellulose, or cellulose esters), regenerated or synthetic keratin membranes, lipid infused synthetic membranes (e.g., such as that used in a parallel artificial membrane permeability assay), PTFE, PVDF, nylon, other synthetic polymer membranes, live human or animal skin, dead human or animal skin (e.g., cadaver skin), or other live or dead tissue portions (e.g., lung or corneal tissue). In some embodiments, the membrane 101 may be formed from or in part from an in vitro cell or tissue culture. In some embodiments, the membrane 101 may have a bulk elastic modulus in a range of about 1 kPa to about 1000 kPa. For example, in some embodiments, the membrane 101 may be made of human skin that has a Young's Modulus in a range of about 25 kPa to about 450 kPa, depending upon a study, an age, a temperature, and a site from which the skin was taken. In some embodiments, the membrane 101 may have pore sizes ranging from a nominal size of about 0.04 nm (100 Daltons) to about 1 μm. The membrane 101 is sized to be contacted along a peripheral edge by the gaskets 128, which are in contact with the frontal plate 126 of the clamp 104 and the main body 102. Accordingly, the membrane 101 typically has a diameter of about 1 cm to about 12 cm (e.g., about 2.5 cm).

In some implementations, the substance may be an aerosolized substance (e.g., a spray, vapor, gas, or mist formulation) or a non-aerosolized substance (e.g., provided in a powder, cream, or gel formulation) that is examined to determine diffusion characteristics that relate to on an effectiveness, a toxicity, or a contamination profile of the substance, or that is examined for interactions with the membrane 101, such as surface binding of tanners, sunscreens, and insect repellants. Example aerosolized substances include inhaled drugs (e.g., nebulizer solutions), airborne nanoparticles used in various applications, cigarette smoke, and other environmental insults, such as pesticides, chemical fumes or vapors, environmental pollutants, electromagnetic insults (e.g., light, radiation, etc.), and other chemical insults. Other example substances included topical drugs (e.g., skin formulations) and other topical chemical compounds, such as skin absorbed toxic substances (e.g., topical VX nerve agent use), and modification materials (e.g., testing of penetration enhancers).

FIG. 11 illustrates a side view of a diffusion system 1000 (e.g., including the diffusion cell 100 and the splash guard 150) as arranged to carry out a diffusion study of an airborne substance 103. The substance 103 can be prepared in a dosage source 105 that delivers fixed doses, such as a syringe pump sprayer (e.g., as shown in FIG. 11), or another metered dose device. The membrane 101 is equilibrated (e.g., via submersion or exposure in a fixed relative humidity chamber) in a volume of a fluid buffer 107 that will be used as a receptor solution to prevent shifting of the membrane 101 that may otherwise occur due to a sudden exposure to the fluid buffer 107. The fluid buffer 107 may be water-based or organic and may be a liquid or a gas. Example fluid buffers 107 include biological mediums (e.g., plasma, serum, blood, cerebrospinal fluid, aqueous humor, etc.), other buffers (e.g., phosphate buffer, phosphate buffered saline, Hank's balanced salt solution, Krebs buffer, cell culture media, etc.), and modifications thereof, which may include surfactants, such as dipalmitoylphosphatidylcholine (DPPC), polysorbate (tween), or other surfactants. A stir bar disposed within the interior recess 116 is activated during the equilibration of the membrane 101. The membrane 101 is placed between the two gaskets 128 of the clamp 104, and the clamp 104 is secured to the main body 102 using the knobs 146 to fix the membrane 101 in place across the open end 114 of the interior chamber 106.

The splash guard 150 may be optionally assembled with the diffusion cell 100, and the diffusion cell 100 is placed in a horizontal orientation atop a surface 109 (e.g., a balance, a heater, a table, a magnetic stir plate, or an automated sampling robot apart from the dosage source 105. The fluid buffer 107 is delivered to the interior chamber 106 using a syringe or another delivery device (e.g., a pipette, a fluid pump, or an automated sampling robot, not shown) via one or more of the sample ports 108, 110, 112. An initial volume of about 0.5 mL to about 1000 mL may be delivered to the interior chamber 106. Any resulting bubbles in the fluid buffer 107 may be removed from the interior chamber 106 by tilting and/or tapping the diffusion cell 100 or by flushing solution through lines connected to the sample ports 108, 110, 112 until the bubbles are removed (e.g., in the case of a flow through study). Any open sample ports 108, 110, 112 are closed with a syringe or another closure device (not shown). The fluid buffer 107 and the membrane 101 may then be equilibrated to a selected temperature of about 20° C. to about 50° C. by flowing a heat transfer fluid through the inlet port 120, the exterior chamber 118, and the outlet port 122. Example heat transfer fluids include water, 10-50% (v/v) propylene glycol or ethylene glycol (e.g., 30% ethylene glycol results in only approximately a 1% loss of thermal conductance in water, a minimal change in viscosity, and acts as a deterrent to fungus, bacteria, and algae growth), and other fluids. The heat transfer fluid is typically flowed for a period of about 5 min to about 1 day, continuously for a duration of the experiment.

Once the fluid buffer 107 and the membrane 101 achieve a selected temperature, the diffusion cell 100 is positioned such that the membrane 101 is located at a distance of about 5 cm to about 32 cm from an exit port 111 of the dosage source 105 and such that a central axis of the main body 102 of the diffusion cell 100 is vertically displaced from a center of the exit port 111 by about 0 cm to about 3 cm. A central axis of the main body 102 may be centrally aligned with or vertically offset from a central axis of a spray of the substance 103, depending on a distance between the membrane 101 and the dosage source 105. For example, the central axis of the main body 102 is approximately aligned with the central axis of the spray at a distance of about 8 inches, whereas the central axis of the main body 102 is vertically offset from the central axis of the spray by about 1 cm to about 2 cm at a distance of about 12 inches. In some implementations, the diffusion cell 100 is then placed into a fitted metallic or polymer holder atop the surface 109. In some examples, the use of polymer holders with low thermal conductivity improves the efficiency of the water jacketing system provided by the exterior chamber 118. In some implementations, 3-4 prong system can be used to hold the diffusion cell in place atop the surface 109.

The substance 103 is ejected (e.g., sprayed) from the dosage source 105 towards the membrane 101 in an aerosolized form, which is determined by experiment-specific parameters and will vary based upon solvent properties. For example, a fixed volume of about 50 µL to about 500 µL of the substance 103 is ejected from the dosage source over a period of about 0.25 s to about 1 s such that about 2 µL/cm$^2$ to about 20 µL/cm$^2$ (e.g., about 10 µL/cm$^2$) of the substance achieves contact with the membrane 101. An upper limit to an amount of substance 103 per area that can be delivered to the membrane 101 depends upon the properties of the solvent and the membrane 101. About 1% to about 100% of the ejected volume may contact the membrane 101, depending on a size of the membrane 101, the distance, a solvent, and dosage source characteristics. In some implementations, about 5% to about 60% of the ejected volume may contact the membrane 101 with an even distribution, according to the particular experimental parameters discussed herein. After the substance 103 is delivered to the membrane 101, the splash guard 150 may be optionally removed from the diffusion cell 100.

A sample volume of about 10 µL to about 5000 µL of the fluid buffer 107 is removed from the interior chamber 106 with a syringe or another removal device at selected intervals that may vary between about 0.5 min and about 240 min over a period of about 5 min to about 1 day (e.g., about 300 min). In some implementations, a volume of the fluid buffer 107 equal to the volume of the fluid buffer 107 that was removed may be delivered to the interior chamber 106 via the same one or more sample ports 108, 110, 112 through which the fluid buffer 107 was removed (e.g., sequentially following the removal) to replenish the fluid buffer 107, and the one or more sample ports 108, 110, 112 are then closed. In some implementations, a volume of the fluid buffer 107 equal to the volume of the fluid buffer 107 that was removed may be delivered to the interior chamber 106 via one or more sample ports 108, 110, 112 that are not used for removal of the fluid buffer 107, while the fluid buffer 107 is being removed from the interior chamber 106 (e.g., in a parallel, flow-through configuration), to replenish the fluid buffer 107, and the sample ports 108, 110, 112 are then closed.

Concentrations of the substance 103 in the samples of the fluid buffer 107 are measured using various analytical techniques following removal of the samples from the interior chamber. Example analytical techniques include photometric methods, such as UV/Visible spectrophotometry, spectrofluorophotometry, and luminomitry. Such methods may be used alone, such as a plate reader or individual cuvettes, or as part of a chromatographic separation, such as HPLC or UPLC. Such methods may also use electrochemical detection. Mass spectrophotometery may also be used coupled with LC (LC/MS) or Gas chromatography (GC/MS). The concentrations and the area of the membrane 101 may be used to compute parameters including suitability of the membrane 101 for certain objectives, a flux, an accumulation, a diffusivity, a permeability coefficient, and a lag time.

The diffusion cell 100 is advantageously configured and, accordingly, particularly useful for in vitro examination of diffusion characteristics of aerosolized substances, which may not be adequately examined using conventional diffusion cells (e.g., Franz diffusion cells, side-by-side diffusion cells, and Valia Chien diffusion cells) that include liquid carrying donor chambers and that accordingly provide liquid-liquid or liquid-membrane-liquid interfaces. For example, in some cases, a substance that is typically aerosolized in its useful form may only be studied using a conventional diffusion cell in a different, non-aerosolized form, such that data obtained from the studies may not accurately represent behaviors of the substance in its useful form. In contrast, an open, accessible configuration of the clamp 104 (e.g., owing in part to the configuration of the central opening 134 and the beveled circular edge 136) of the diffusion cell 100 provides an air-solid interface (e.g., an interface defined by the solid membrane 101 and an ambient air environment) to a which volume of aerosolized substance can be delivered with a substantially even distribution across an area of the membrane 101. In some examples, an even distribution of a substance across a membrane is taken as an underlying assumption for diffusion cell experiments, such that results obtained from the experiments may not accurately represent a true behavior of the substance in a realistic application if the substance is not evenly distributed across the membrane. The configuration of the diffusion cell 100 advantageously facilitates such an even distribution and thereby allows realistic, representative data to be obtained from experiments.

Furthermore, the configuration of the diffusion cell 100 and the horizontal experimental arrangement of the diffusion cell 100 advantageously permit examination of an aerosolized substance using only a small volume per unit area of the membrane 101, which may be beneficial when the substance is only available in limited amounts or is obtained at a high cost. For example, the methods discussed herein may achieve a distribution of about 10 µL/cm$^2$ when ejecting a sample volume of about 200 µL the substance. In contrast, conventional diffusion cells typically require a significantly larger sample volume in order to achieve an even distribution of substance on a membrane. Additionally, the horizontal experimental arrangement of the diffusion cell 100 and the flat surface of the frontal plate 126 can prevent an aerosolized substance from settling and pooling on the membrane 101, which may otherwise occur with vertical experimental arrangements or conventional donor chamber structures employed for conventional diffusion cells. Another significant benefit of the diffusion cell 100 and the associated methods discussed above is drying of the small volume of the substance 103 on the surface of the membrane 101. A loss of solvent due to the drying can drastically change the diffusivity of the test substance 103.

FIG. 12 illustrates an example process 200 for performing a diffusion test using the diffusion cell 100. In some implementations, the process includes clamping a membrane (e.g., the membrane 101) to a body (e.g., the main body 102) such that a first surface of the membrane is in fluid communication with an interior chamber (e.g., the interior chamber 106) of the body and a second surface of the membrane is exposed to ambient air (202). In some implementations, the process further includes flowing a substance through the ambient air such that at least a portion of the substance lands on the second surface while the membrane is vertically oriented (204). In some implementations, the process further includes determining a concentration of the substance in the interior chamber after some of the substance has diffused through the membrane (206).

Figure 13A:
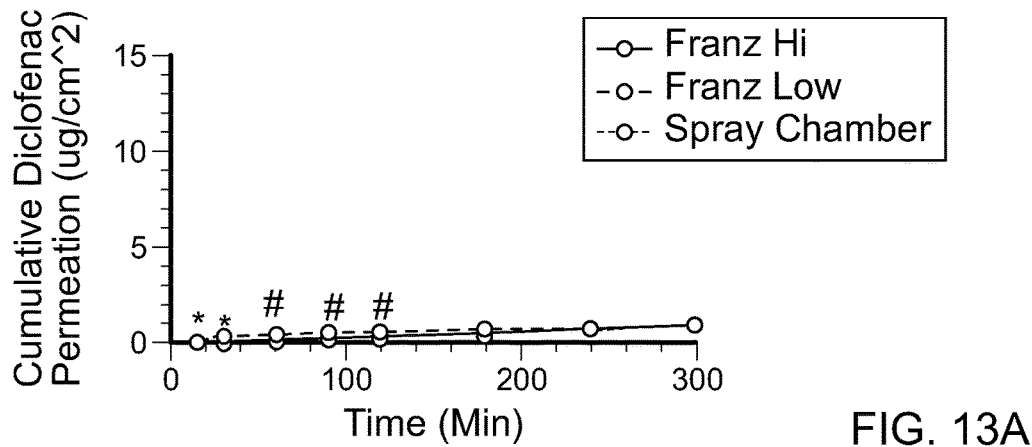
FIGS. 13A-13F provide a set of graphs that illustrate permeation as a function of time for a drug substance tested with a liquid spray application using the diffusion cell of FIG. 1 and the same drug substance tested with bulk liquid applications using conventional diffusion cells.
Figure 13B:
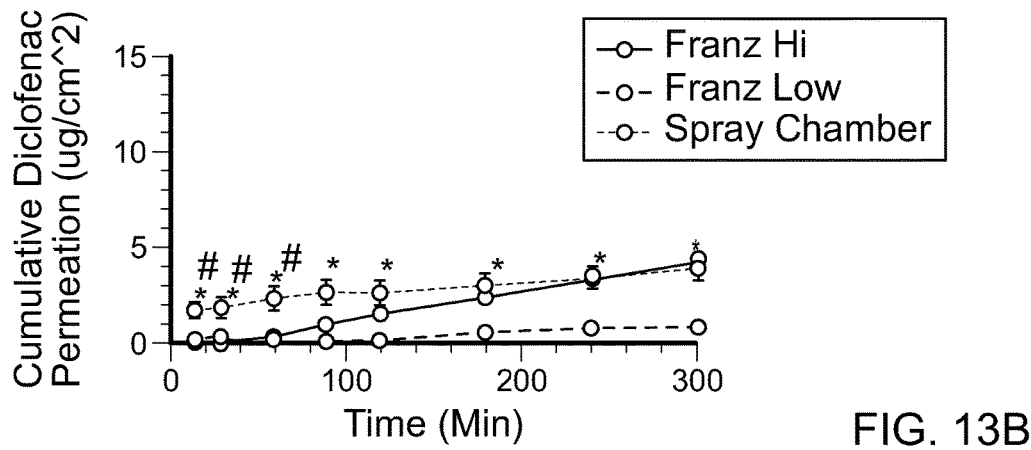
Figure 13C:
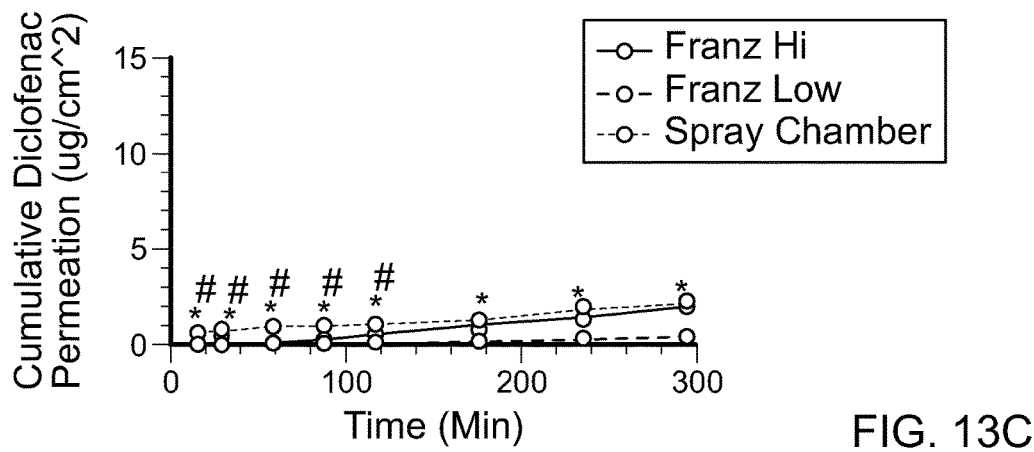
Figure 13D:
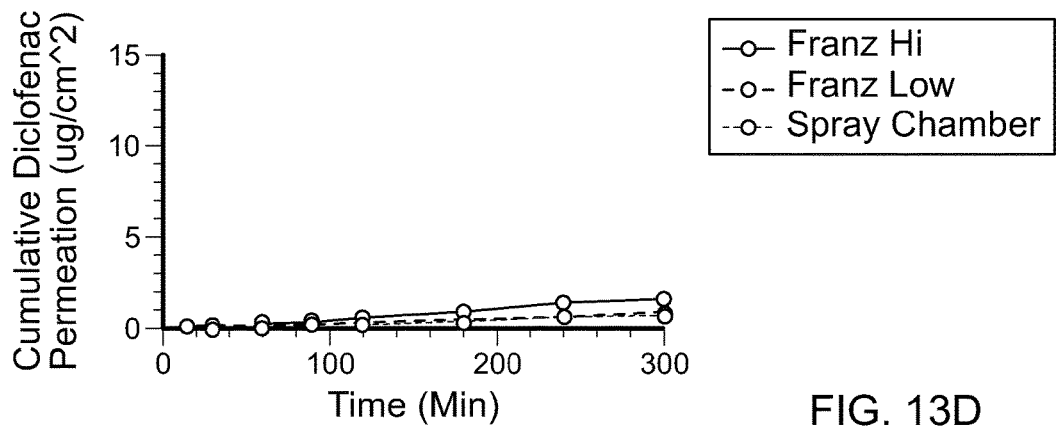
Figure 13E:
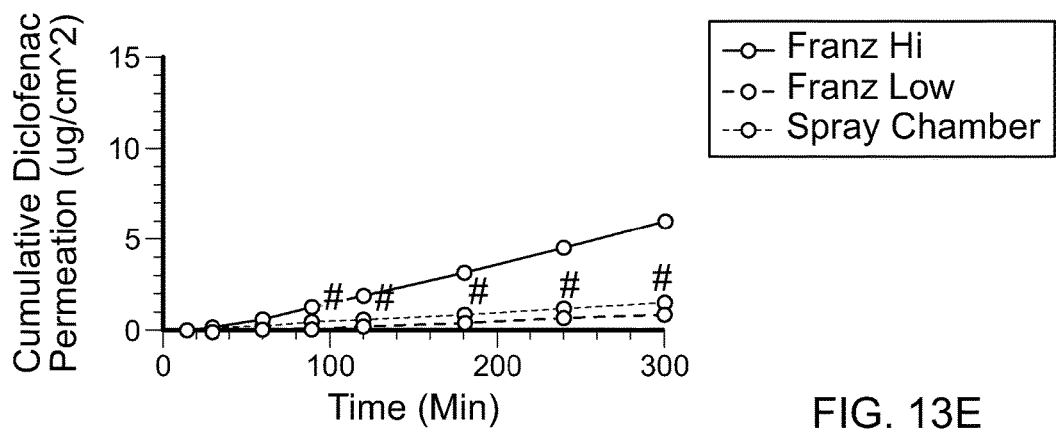
Figure 13F:
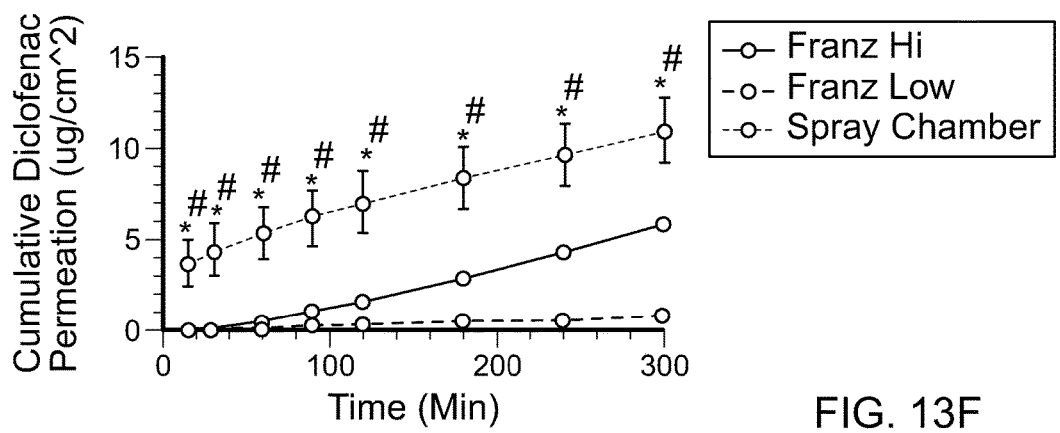

FIGS. 13A-13F provide a set of graphs that illustrate permeation as a function of time for a drug substance tested with a liquid spray application using the diffusion cell 100 (Spray Chamber), the same drug substance tested with a bulk liquid application using a conventional Franz diffusion cell (Franz Hi), and the same drug substance diluted 1:10 in deionized water, tested with a bulk liquid application using a conventional Franz diffusion cell (Franz Low). In the example experiments, diclofenac sodium was allowed to diffuse through a snake skin model (e.g., a membrane made of shed snake skin) for an outermost epidermis layer (e.g., stratum corneum) over 5 hours at room temperature (FIGS. 13A, 13B, and 13C) and at 32° C. (FIGS. 13D, 13E, and 13F). The diclofenac was tested in three different formulations that each contained approximately 4% (w/v) diclofenac sodium. The first formula (FIGS. 13A and 13D) consisted of 4% (w/v) aqueous diclofenac sodium. The second formula (FIGS. 13B and 13E) was a generic diclofenac formulation consisting of diclofenac sodium (aqueous 4% (w/v), isopropanol (25% v/v), propylene glycol (1.5% w/v), and soy lecithin (HLB 7, 1% w/v). The second formula was made by first dissolving soy lecithin into water. Isopropanol and propylene glycol were then added to the solution and mixed to homogeneity. Diclofenac sodium was weighed into a volumetric flask and brought to volume using the soy lecithin solution. This was then ultrasonicated in a bath sonicator (35 watt Fisher Scientific) for 30 minutes to dissolve the diclofenac immediately prior to use. The third formula (FIGS. 13C and 13F) was the commercially available formulation Voltaren (4% w/v diclofenac). Due to the difference in applied substance volume (100 µL) in the Franz chambers, versus 10 µL for the diffusion cell 100, the three systems were examined using solutions of the same concentration (40 mg/mL diclofenac), and the same total amount of drug was applied (4 mg/mL diclofenac).

Spray volume calculations showed that during the experiments using the diffusion cell 100, 10.09±1.22 µL/cm$^2$ (n=10) and 5.06±1.87 µL/cm$^2$ (n=6) of the diclofenac sodium formulation was delivered at a substantially even distribution to the membrane when 200 µL and 100 µL of the diclofenac sodium formulation, respectively, were sprayed from 3 mL syringes at a distance of about 8 inches from the membrane, illustrating a regularity of the system. Such delivery volumes meet standard, accepted guidelines of 10-12 µL per cm$^2$ of skin surface for finite dose in vitro testing of skin absorption/permeability. In contrast, the high and low concentration Franz diffusion cells required delivery of about 100 µL of the diclofenac sodium formulation to the membrane to achieve an even distribution across the membrane. Accordingly, the diffusion cell 100 was able to be utilized with about ten times less the amount of substance as required for the conventional Franz diffusion cells.

As shown in the graphs of FIGS. 13E and 13F, the conventional Franz diffusion cells could not distinguish the permeability of diclofenac sodium between the generic formulation and the commercial formulation, whereas the diffusion cell 100 did show a difference in permeability of diclofenac sodium between the generic formulation and the commercial formulation. In this regard, the diffusion cell 100 can distinguish certain differences that cannot be distinguished by the Franz diffusion cells. Accordingly, the diffusion cell 100 can be used to test a substance via a regular, useful aerosol delivery in a biologically relevant range for topical skin applications.

A number of embodiments and implementations have been described above. However, it will be understood that various modifications may be made without departing from the spirit and scope of the disclosure to accommodate various substance characteristics or other requirements (e.g., a low substance availability, a high substance or membrane cost, a micro-dialysis-based receiver chamber, a low substance detectability, etc.).

For example, while the diffusion cell 100 and the splash guard 150 have been described and illustrated as including certain dimensions, shapes, and material formulations, in some embodiments, diffusion cells and splash guards that are similar in one or both of construction and function to the diffusion cell 100 and the splash guard 150 may include one or more components that have different dimension, shapes, and/or material formulations.

While the diffusion cell 100 has been described and illustrated as including the three sample ports 108, 110, 112, in some embodiments, a diffusion cell that is similar in construction and function to the diffusion cell 100 may include a different number or a different type of sample ports.

While the diffusion cell 100 has been described and illustrated as including the exterior chamber 118 as a water jacket, in some embodiments, a diffusion cell that is similar in function to the diffusion cell 100 may not include an exterior chamber.

While the frontal plate 126 of the adjustable plate has been described and illustrated as a flat plate with a flat central opening 134, in some embodiments, a diffusion cell includes an adjustable clamp that has a curved frontal plate that may have a curved opening for specialized biological or synthetic membranes, such as a cornea or a contact lens. Such diffusion cells may also include a body that has a corresponding curved central opening.

Figure 14:
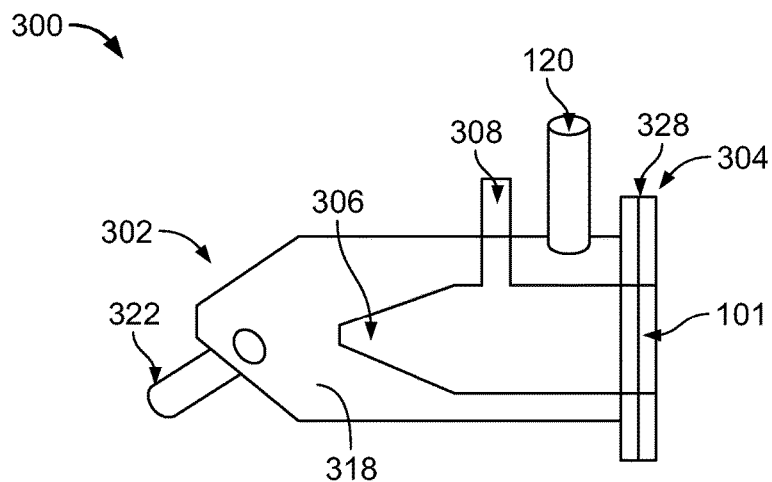
FIG. 14 is a side schematic view of a diffusion cell.
Figure 15:
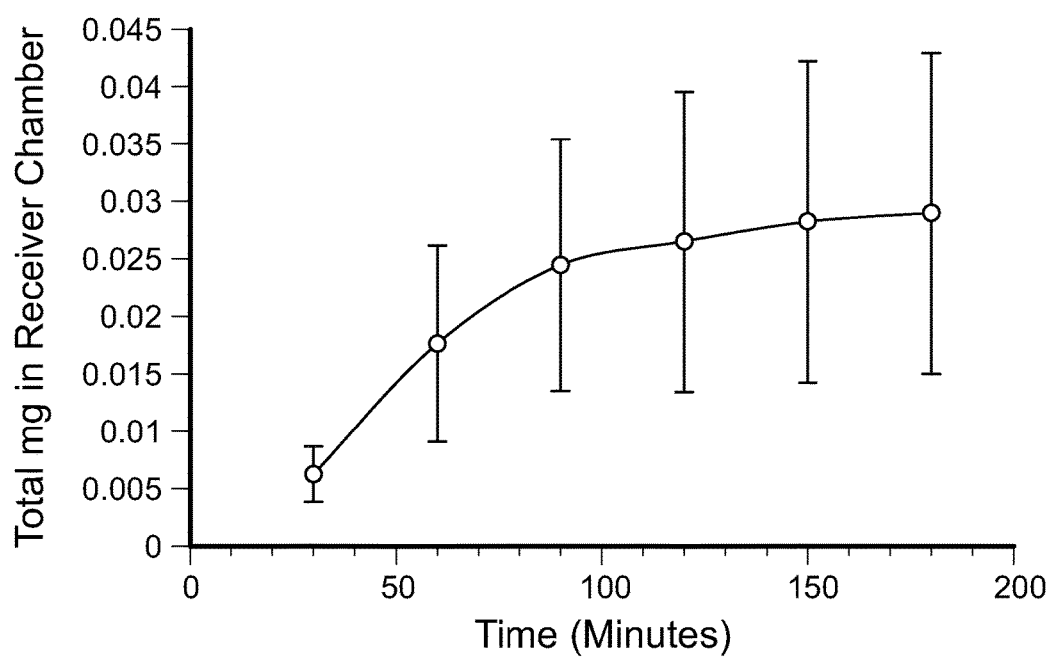
FIG. 15 is a graph that illustrates accumulation of a substance through a membrane assembled with the diffusion cell of FIG. 14.

In some embodiments, a diffusion cell that is similar in construction and function to the diffusion cell 100 can be used to perform diffusion tests on airborne substances, such as the methods described above with respect to the diffusion cell 100. For example, FIG. 14 is a side schematic view of a diffusion cell 300 that includes a main body 302, an adjustable clamp 304 including a cover plate 326, an interior chamber 306, an exterior chamber 318, an inlet port 320, an outlet port 322, a sample port 308, and silicon gaskets 328. FIG. 15 provides a graph that illustrates accumulation of a substance (e.g., Blue #1 dye in water) through a 2 kDa molecular weight cut-off cellulose ester dialysis membrane. During the test, 3.1±0.91 µL/cm² (n=10) was delivered to the membrane.

Figure 16:
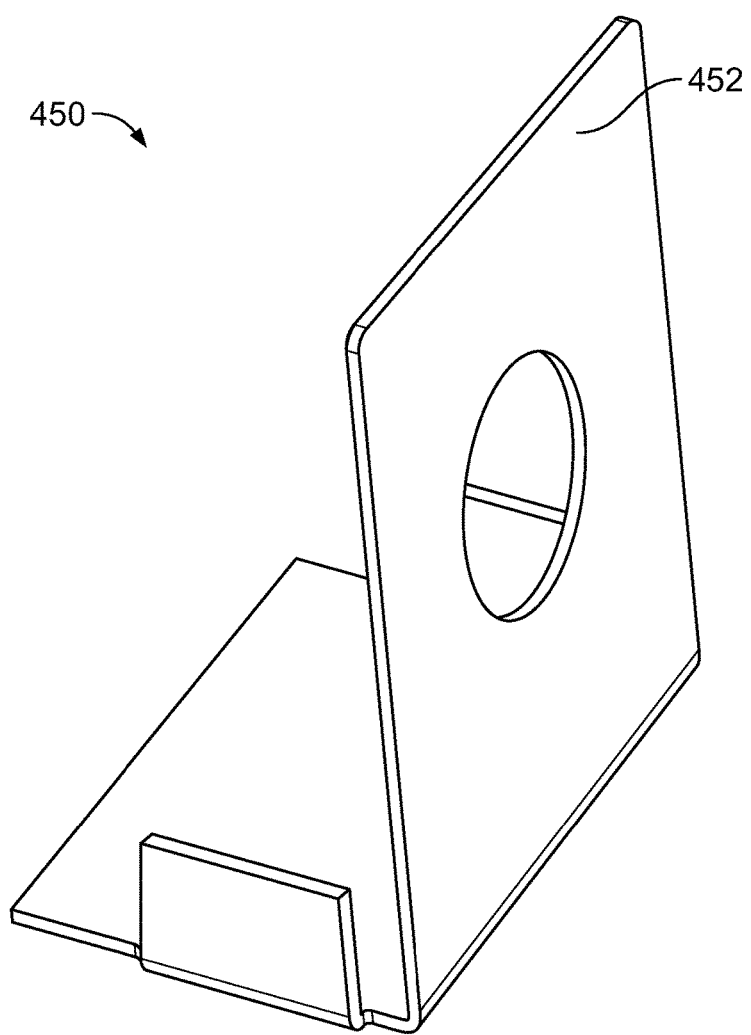
FIG. 16 is a perspective view of a splash guard that can be attached to the diffusion cell of FIG. 1 or FIG. 14.

FIG. 16 illustrates an alternative splash guard 450 that is similar in construction and function to the splash guard 150 and that can be assembled with the diffusion cell 100 or with another diffusion cell to block contamination of the sample area of the body of the diffusion cell. The splash guard 450 is similar in construction and function to the splash guard 150, except that the splash guard 450 has a narrower, shorter frontal plate 452 that does not include lateral openings for engaging fastening assemblies of a diffusion cell.

While the methods of using the diffusion cell 100 have been described and illustrated with the diffusion cell 100 arranged in a horizontal orientation, in some implementations, the diffusion cell 100 is arranged in a vertical orientation to perform a diffusion test.

While the methods of using the diffusion cell 100 have been described with respect to certain volumes, time points, and ordered sequences of events, in some implementations, the diffusion cell 100 is used to perform diffusion tests including different volumes, times points, and sequences of events.

Additionally, other embodiments and implementations are within the scope of the following claims.

What is claimed is:

1. A method of performing a diffusion test, comprising:
   clamping a membrane to a body of a diffusion cell such that the membrane is positioned along a plate of the diffusion cell, such that a first surface of the membrane is in fluid communication with an interior chamber of the body, and such that a second surface of the membrane is exposed to ambient air;
   flowing a substance through the ambient air along a flow path that narrows towards the membrane through a tapered opening of the plate, such that a first portion of the substance lands on the second surface of the membrane and a second portion of the substance collects on the tapered opening of the plate while the membrane is vertically oriented;
   flowing the second portion of the substance away from the membrane and along the tapered opening to prevent the second portion of the substance from pooling on the membrane; and
   determining a concentration of the substance in the interior chamber after some of the substance has diffused through the membrane.

2. The method of claim 1, further comprising arranging the body in a horizontal orientation prior to flowing the substance through ambient air.

3. The method of claim 1, further comprising assembling a splash guard with the body to prevent an airborne flow of the substance from contacting the body.

4. The method of claim 1, wherein clamping the membrane to the body comprises providing an air-solid interface that is oriented perpendicular to a longitudinal axis of the body.

5. The method of claim 1, wherein flowing the substance through the ambient air comprises flowing the substance horizontally towards the membrane such that the first portion of the substance lands on the membrane in a substantially even distribution across the second surface of the membrane.

6. The method of claim 1, further comprising distributing a volume of about 2 µL/cm² to about 20 µL/cm² of the substance across the second surface of the membrane.

7. The method of claim 1, further comprising flowing a heat transfer fluid through an exterior chamber of the body that surrounds the interior chamber of the body.

8. The method of claim 1, further comprising delivering a fluid buffer to the interior chamber of the body.

9. The method of claim 8, further comprising introducing the fluid buffer into a port located above the interior chamber of the body.

10. The method of claim 8, further comprising withdrawing a sample of the fluid buffer from the interior chamber of the body at multiple predetermined times after the first portion of the substance has landed on the second surface of the membrane.

11. The method of claim 10, wherein determining the concentration of the substance in the interior chamber comprises determining respective concentrations of the substance in the fluid buffer following the multiple predetermined times.

12. The method of claim 11, further comprising determining one or more diffusion parameters associated with one or both of the substance and the membrane based on the respective concentrations.

13. The method of claim 1, wherein flowing the substance through the ambient air comprises flowing an aerosolized substance towards the membrane.

14. The method of claim 1, wherein flowing the substance through the ambient air comprises spraying the substance towards the membrane.

15. The method of claim 1, wherein flowing the substance through the ambient air comprises flowing nanoparticles towards the membrane.

16. The method of claim 1, wherein flowing the substance through the ambient air comprises flowing a drug towards the membrane.

17. The method of claim 1, wherein flowing the substance through the ambient air comprises flowing a chemical that is toxic to animals towards the membrane.

18. The method of claim 1, wherein clamping the membrane to the body comprises securing a construct comprising one or both of an artificial tissue and a natural tissue to the body.

19. The method of claim 1, further comprising:
   flowing the substance through the ambient air in a first direction along the flow path that narrows towards the membrane; and
   flowing the second portion of the substance away from the membrane and along the tapered opening in a second direction that is different from the first direction to prevent the
      second portion of the substance from pooling on the membrane.

20. A diffusion cell, comprising:
   a body defining an interior chamber; and
   an adjustable clamp configured to secure a membrane to the body across an open end of the interior chamber,
   wherein the adjustable clamp comprises a plate that defines a beveled edge,
   wherein the beveled edge is configured to narrow an airflow path of a substance towards the body, and
   wherein the beveled edge is configured to facilitate flow of the substance along the beveled edge and away from the membrane to prevent pooling of the substance on the membrane.

* * * * *

UNITED STATES PATENT AND TRADEMARK OFFICE
CERTIFICATE OF CORRECTION

PATENT NO. : 10,613,011 B2
APPLICATION NO. : 15/457730
DATED : April 7, 2020
INVENTOR(S) : Daniel Munt et al.

Page 1 of 1

It is certified that error appears in the above-identified patent and that said Letters Patent is hereby corrected as shown below:

On the Title Page

Item (60), Column 1 (Related U.S. Application Data), Line 2, Delete "4, 2016." and insert -- 14, 2016. --, therefor.

Signed and Sealed this
Thirteenth Day of October, 2020

Andrei Iancu
*Director of the United States Patent and Trademark Office*